(12) United States Patent  
Huang et al.

(10) Patent No.: US 9,402,541 B2  
(45) Date of Patent: Aug. 2, 2016

(54) OPTICAL DEVICE FOR CORNEAL MEASURING AND METHOD FOR CORNEAL MEASURING

(71) Applicants: CRYSTALVUE MEDICAL CORPORATION, Gueishan Township, Taoyuan County (TW); Sheng-Lung Huang, Taipei (TW)

(72) Inventors: Sheng-Lung Huang, Taipei (TW); William Wang, Taoyuan (TW); Tuan-Shu Ho, Taipei (TW); Chung-Ping Chuang, Gueishan Township, Taoyuan County (TW); Meng-Shin Yen, Taipei (TW); Kuang-Yu Hsu, Taipei (TW); Chien-Chung Tsai, Taipei (TW); Chung-Cheng Chou, Luzhu Township, Taoyuan County (TW)

(73) Assignees: CRYSTALVUE MEDICAL CORPORATION, Gueishan Township, Taoyuan County (TW); Sheng-Lung Huang, Taipei (TW)

( * ) Notice: Subject to any disclaimer, the term of this patent is extended or adjusted under 35 U.S.C. 154(b) by 0 days.

(21) Appl. No.: 14/554,055

(22) Filed: Nov. 26, 2014

(65) Prior Publication Data

US 2015/0164316 A1 Jun. 18, 2015

(30) Foreign Application Priority Data

Dec. 13, 2013 (TW) .............................. 102146009 A

(51) Int. Cl.  
*A61B 3/14* (2006.01)  
*A61B 3/00* (2006.01)  
*A61B 3/107* (2006.01)

(52) U.S. Cl.  
CPC ....................................... *A61B 3/107* (2013.01)

(58) Field of Classification Search  
USPC .................................................. 351/200–246  
See application file for complete search history.

(56) References Cited

U.S. PATENT DOCUMENTS

| 6,755,819 B1* | 6/2004 | Waelti | A61F 9/00804 606/4 |
| 8,226,235 B2* | 7/2012 | Roberts | A61B 3/165 351/210 |
| 2011/0157551 A1* | 6/2011 | Plamann | A61B 3/103 351/206 |

* cited by examiner

*Primary Examiner* — Mohammed Hasan  
(74) *Attorney, Agent, or Firm* — Cheng-Ju Chiang

(57) ABSTRACT

An optical device for corneal measuring includes a light source module, a first optical module, a second optical module including a reference mirror, a light splitter and an image analysis unit. The light of the light source module is transmitted to the first and second optical modules through the light splitter. The light is transmitted to a cornea through the light splitter and the first optical module and reflected by the cornea to form a first light, the light is transmitted to the reference mirror through the light splitter and reflected by the reference mirror to form a second light. The first and second lights are transmitted to the light splitter and the image analysis unit. The reference mirror moves along a first direction, and when the first light and the second light interfere with each other, a relative optical path length is obtained.

13 Claims, 5 Drawing Sheets

OPTICAL DEVICE FOR CORNEAL MEASURING AND METHOD FOR CORNEAL MEASURING

CROSS REFERENCE TO RELATED APPLICATIONS

This Non-provisional application claims priority under 35 U.S.C. §119(a) on Patent Application No(s). 102146009 filed in Taiwan, Republic of China on Dec. 13, 2013, the entire contents of which are hereby incorporated by reference.

BACKGROUND OF THE INVENTION

1. Field of Invention

The invention relates to a device and method for medical detection and, in particular, to a device and method detecting cornea through optics.

2. Related Art

A corneal measuring instrument is a kind of optical device for measuring the corneal surface, and after the profile of the corneal surface is acquired, the contact lenses can be designed to fit different users. Besides, the corneal profile also can present some ocular diseases. Hence, the corneal profile can be applied to the preoperative assessment and postoperative corneal recovery in the surgical procedure of RK, PK or LASIK. Therefore, an accurate corneal profile is very important for the following treatment.

FIG. 1 is a schematic diagram of a conventional optical image device for the corneal measuring.

The optical device 1 in FIG. 1 includes an image projector 10, a positioning light source 12, a measuring light source 14 and an image processing unit 16. The image projector 10 can provide an image for the target to be measured and the target to be measured needs to continuously see the image, so that the cornea 18 of the target can be positioned and the measurement error caused by the displacement during the measuring process can be avoided. Then, the positioning light source 12 can provide a light beam that is transmitted to the cornea 18, and the light beam is reflected to enter the receiving end of the image processing unit 16. Through the reflected light beam of the positioning light source 12, the image processing unit 16 can be adjusted into a better measuring state to increase the measurement accuracy.

In the actual measuring, the measuring light source 14 can provide a plurality of concentric-circle light beams for the cornea, and the profile of the corneal surface (i.e. curvature) can be determined by the deviation situation of the reflected light beams.

However, this kind of optical device just can generate the profile of the upper corneal surface but can't measure the total thickness of the cornea accurately. In order to measure the corneal thickness, a side light source is generally added in to provide a light beam obliquely entering the cornea, and the side corneal profile can be detected by the reflection of the light beam. Nevertheless, this kind of method still can't accurately measure the real profile of the lower corneal surface.

Therefore, it is an important subject to provide an optical device and method which can measure the upper and lower corneal surfaces to provide a stereoscopic corneal image.

SUMMARY OF THE INVENTION

In view of the foregoing subject, an objective of the invention is to provide an optical device and method which can measure the upper and lower corneal surfaces to provide a stereoscopic corneal image.

To achieve the above objective, an optical device for corneal measuring of the invention includes a light source module, a first optical module, a second optical module including a reference mirror, a light splitter and an image analysis unit.

Through the light splitter, the light provided by the light source module is transmitted to the first optical module and the second optical module.

The light of the light source module is transmitted to a cornea through the light splitter and the first optical module and reflected by the cornea to form a first light, and the first light is sequentially transmitted to the light splitter and the image analysis unit.

The light of the light source module is transmitted to the reference mirror of the second optical module through the light splitter and reflected by the reference mirror to form a second light, and the second light is sequentially transmitted to the light splitter and the image analysis unit.

The reference mirror can move along a first direction, and when the first light and the second light interfere with each other, a relative optical path length is obtained.

In one embodiment, the image analysis unit includes an image shooting unit. The image shooting unit is a charge-coupled device (CCD) camera or a complementary metal-oxide-semiconductor (CMOS) camera.

In one embodiment, the first optical module includes a reflector and a lens, the light of the light source module is sequentially transmitted to the reflector and the lens of the first optical module through the light splitter.

In one embodiment, the reference mirror is movable in a reciprocating manner.

In one embodiment, the reference mirror is a non-spherical mirror or a lens coated with a film.

A method for corneal measuring is also disclosed in this invention and at least comprises the steps of: providing a light transmitted to a first optical module and another light transmitted to a second optical module including a reference mirror.

The method further comprises the step of: dividing a cornea into a plurality of capture regions along a second direction; and transmitting the light to the cornea through the first optical module and sequentially measuring the capture regions.

The measuring steps include: concentrating the light on a first capture surface of the capture region; the light reflected by the first capture surface to form a first light; the another light reflected by the reference mirror to form a second light; and coupling the first light and the second light.

The measuring steps further include: moving the reference mirror along a first direction which is perpendicular to the second direction.

The measuring steps further include: when the first light and the second light interfere with each other, stopping the movement of the reference mirror and acquiring a relative optical path length between the first light and the second light and defining it as a first height.

The measuring steps further include: adjusting the first optical module, so that the light is concentrated on a second capture surface of the capture region, wherein the first capture surface and the second capture surface are disposed along the first direction; the light reflected by the second capture surface to form a third light; moving the reference mirror along the first direction.

The measuring steps further include: when the second light and the third light interfere with each other, stopping the movement of the reference mirror, and acquiring a relative optical path length between the second light and the third light and defining it as a second height.

After measuring the capture regions, the method further comprises the steps of: superposing the first heights of the capture regions to form a first surface; superposing the second heights of the capture regions to form a second surface; and superposing the first surface and the second surface to form a corneal stereoscopic image.

In one embodiment, the step of superposing the first heights of the capture regions to form a first surface further includes a step of: superposing the first heights to form the first surface by an interpolation method.

In one embodiment, the step of superposing the second heights of the capture regions to form a second surface further includes a step of: superposing the second heights to form the second surface by an interpolation method.

In one embodiment, the width of the capture region is between 0.1 μm and 0.25 μm.

In one embodiment, the image analysis unit includes an image shooting unit. The image shooting unit is a charge-coupled device (CCD) camera or a complementary metal-oxide-semiconductor (CMOS) camera.

In one embodiment, the first optical module includes a reflector and a lens, the light of the light source module is sequentially transmitted to the reflector and the lens of the first optical module through the light splitter.

In one embodiment, the reference mirror is movable in a reciprocating manner.

In one embodiment, the reference mirror is a non-spherical mirror or a lens coated with a film.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

To be noted, in the following embodiments and figures, the elements and steps not directly related to this invention are omitted and not shown, and besides, the dimensional relationship between the elements in the figures is just for the easier understanding and not meant to be construed in a limiting sense.

The human cornea is composed of three layers: the outermost corneal epithelium constituted by multi-layer non-keratinized epithelium, the middle and the widest substrate, and the innermost single-layer endothelium constituted by single-layer cell.

The corneal epithelium takes 10% of the total corneal thickness and is constituted by the cell of several layers acting as the protection against the external factor. The substrate is composed of 200~250 sheets of collagen fiber which are parallelly arranged on the corneal surface and takes 90% of the total corneal thickness. The single-layer endothelium is a single cell layer, and includes single-layer cuboid cell forming hexagonal chimera and keeps the tissue transparency by controlling the hydration of the substrate.

The topography of the corneal surface of the most people is a non-spherical body, so the curvature of the corneal surface can't be expected and lacks the uniform rate of change. Hence, how to accurately measure the cornea and adjust the operational parameter according to different measured targets is getting more important.

As below, the optical device and method applied to the corneal measuring of an embodiment of the invention will be illustrated.

Figure 1:
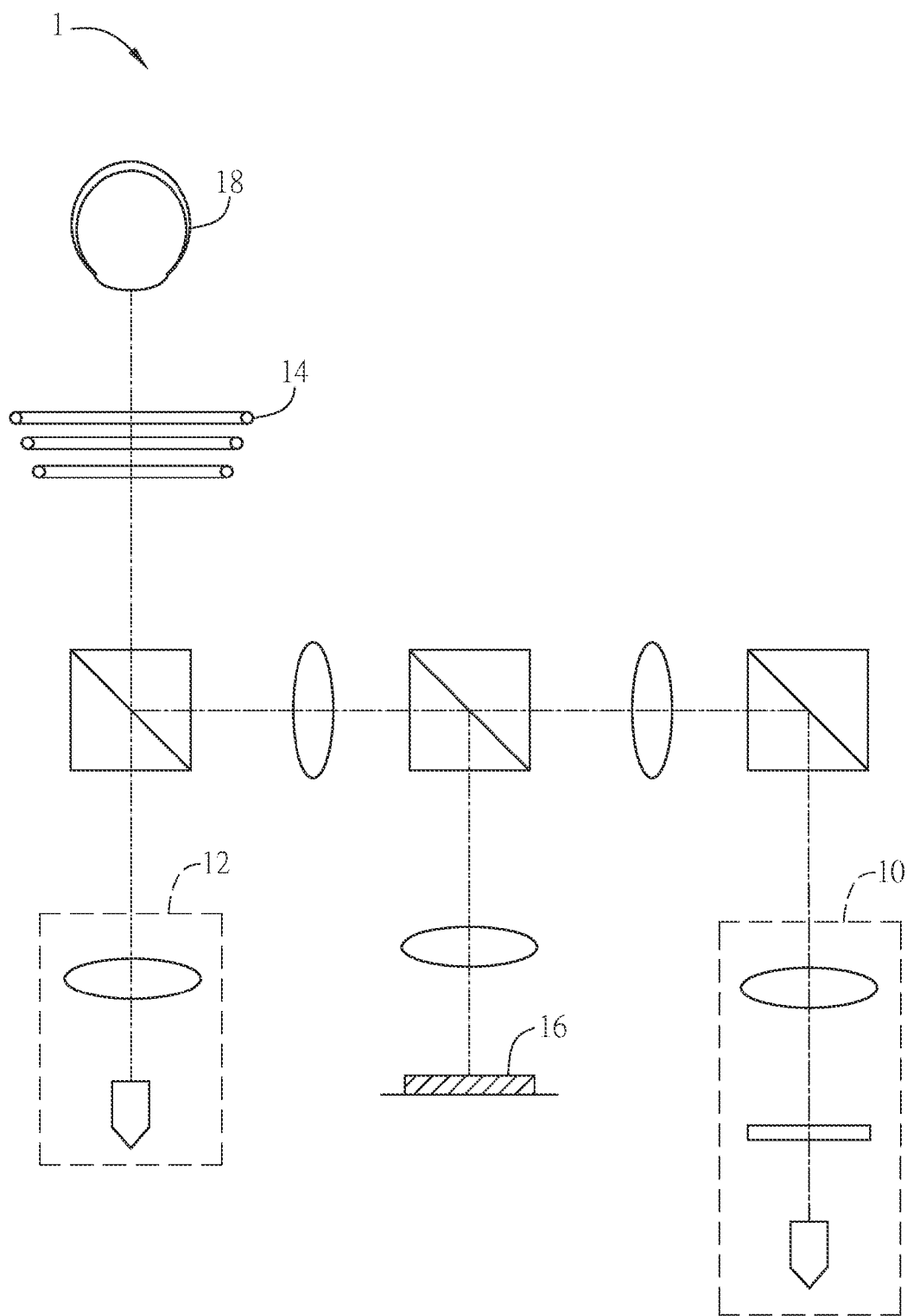
FIG. 1 is a schematic diagram of a conventional optical image device for the corneal measuring.
Figure 2:
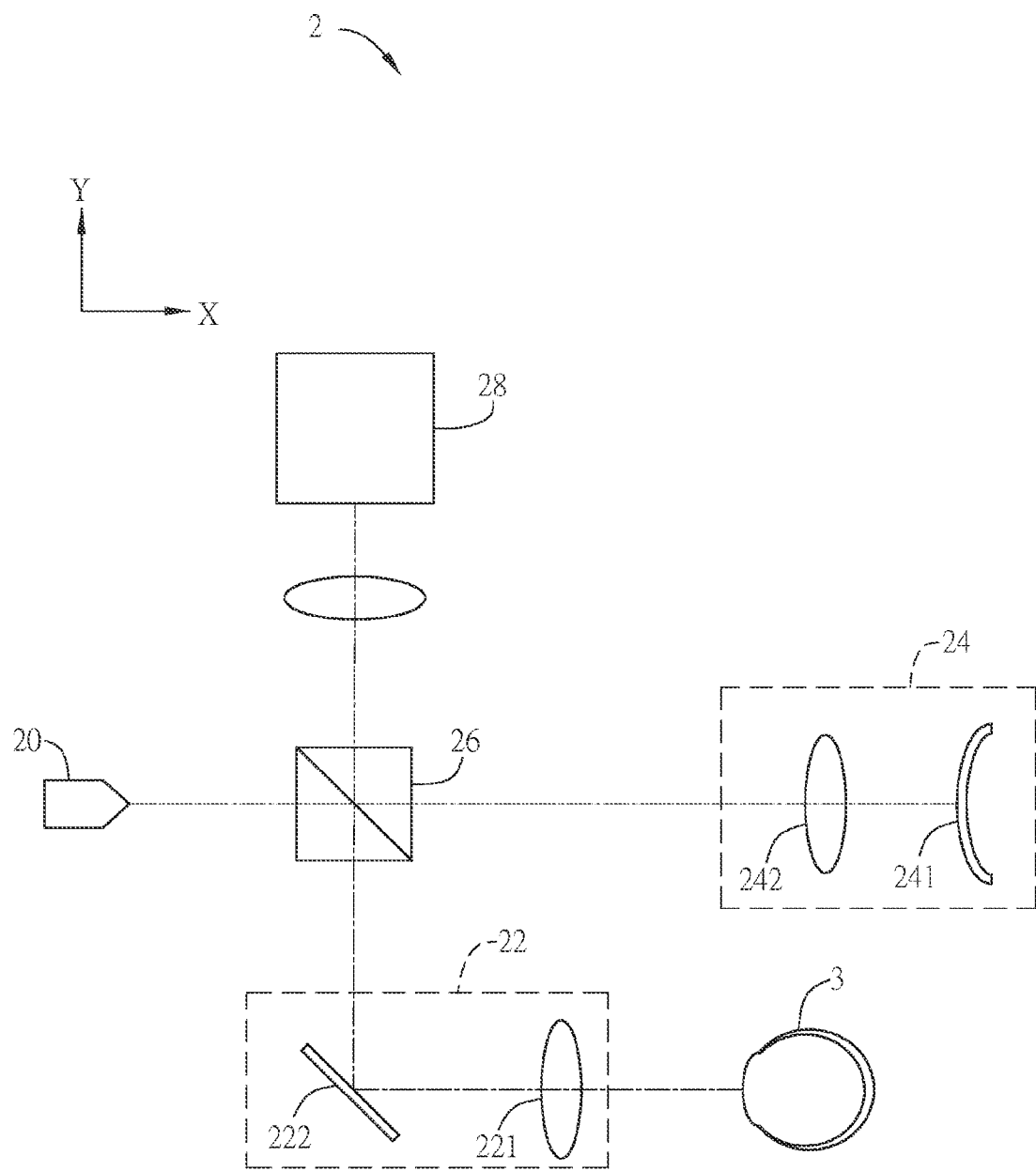
FIG. 2 is a schematic diagram of the optical device of the first embodiment of the invention.

First, refer to FIG. 2, which is a schematic diagram of the optical device of the first embodiment of the invention.

The optical device 2 of this embodiment includes a light source module 20, a first optical module 22, a second optical module 24, a light splitter 26 and an image analysis unit 28.

The light source module of this embodiment can provide a light and can be a wideband laser light source (for example, the center wavelength of the light source is about 1030 nm with a bandwidth of 20-40 nm, also not limited to the invisible light). The wideband laser light source can be embodied by a narrowband laser light source emitting light into an exciting material, but this invention is not limited thereto.

The first optical module 22 is used to concentrate the light provided by the light source module 20 on the cornea 3. Moreover, the first optical module 22 of this embodiment can include a reflector 222 and a lens 221.

The second optical module 24 is used to provide a reference light. The second optical module 24 of this embodiment includes a reference mirror 241. The second optical module 24 further includes a lens 242, which can concentrate and focus the light of the light source module 20 on the reference mirror 241. Besides, the reference mirror of this embodiment can do a reciprocating motion (by a transmission platform for example), especially along the first direction (X direction). In addition to moving the reference mirror 241, both of the reference mirror 241 and the lens 242 can be moved in another embodiment. In other words, the second optical module 24 can move as a whole body to achieve similar effect.

The reference mirror 241 can be a non-spherical mirror or a lens coated with a film. The curvature of the reference mirror 241 needs to match the curvature of the cornea 3 (but the two are unnecessarily the same). Favorably, the curvature radius of the reference mirror 241 can be between 5 mm and 10 mm.

The image analysis unit 28 can be used to analyze and construct the stereoscopic image of the cornea. The image analysis unit 28 of this embodiment can include an image shooting unit. For example, the image shooting unit can be a charge-coupled device (CCD) camera or a complementary metal-oxide-semiconductor (CMOS) camera. Therefore, the image shooting unit can shoot the panoramic image around the eyeball, and the image of this embodiment particularly can be the corneal image of the eyeball.

The light splitter 26 of this embodiment can transmit a part of the light of the light source module 20 to the first optical module 22 and the other part of the light source module 20 to the second optical module 24. In this embodiment, the 50% light will be reflected into the first optical module 22 and the other 50% light will enter the second optical module 24.

As shown in FIG. 2, in the practical operation, the light of the light source module 20 can be transmitted to the cornea 3 through the light splitter 26 and the first optical module 22 and then reflected by the cornea 3 to form a first light. Then, the first light will be transmitted to the light splitter 26 and the image analysis unit 28 sequentially.

In detail, the light splitter 26 of this embodiment reflects the half light to the reflector 222 of the first optical module 22, and then the light is reflected by the reflector 222 and focused on the cornea 3 by the lens 221. Subsequently, the light is reflected by the cornea 3 to form the first light. Moreover, the first light will be transmitted to the light splitter 26 through the lens 221 and the reflector 222 and then transmitted to the image analysis unit 28 through the light splitter 26.

A part of the light of the light source module 20 will enter the first optical module 22, and another part of the light will be transmitted to the second optical module 24. The light of the light source module 20 is transmitted to the reference mirror 241 of the second optical module 24 through the light splitter 26.

In detail, the remaining light not reflected by the light splitter 26 will pass through the light splitter 26 and enter the second optical module 24, and is then concentrated and focused on the reference mirror 241 by the lens 242. Besides, the light will form the second light after being reflected by the reference mirror 241. The second light will be transmitted to the image analysis unit 28 through the lens 242 and the light splitter 26.

The reference mirror 241 can move along the first direction (X direction) (by a transmission platform for example). When the first light and the second light interfere with each other, a relative optical path length (optical path difference, OPD) between the first and second lights can be recorded, and the stereoscopic image of the cornea 3 can be plotted and constructed by the above relative optical path length and the related calculation. The plot scheme can be performed by the calculation of interferometric surface profiling, but this invention is not limited thereto.

Figure 3A:
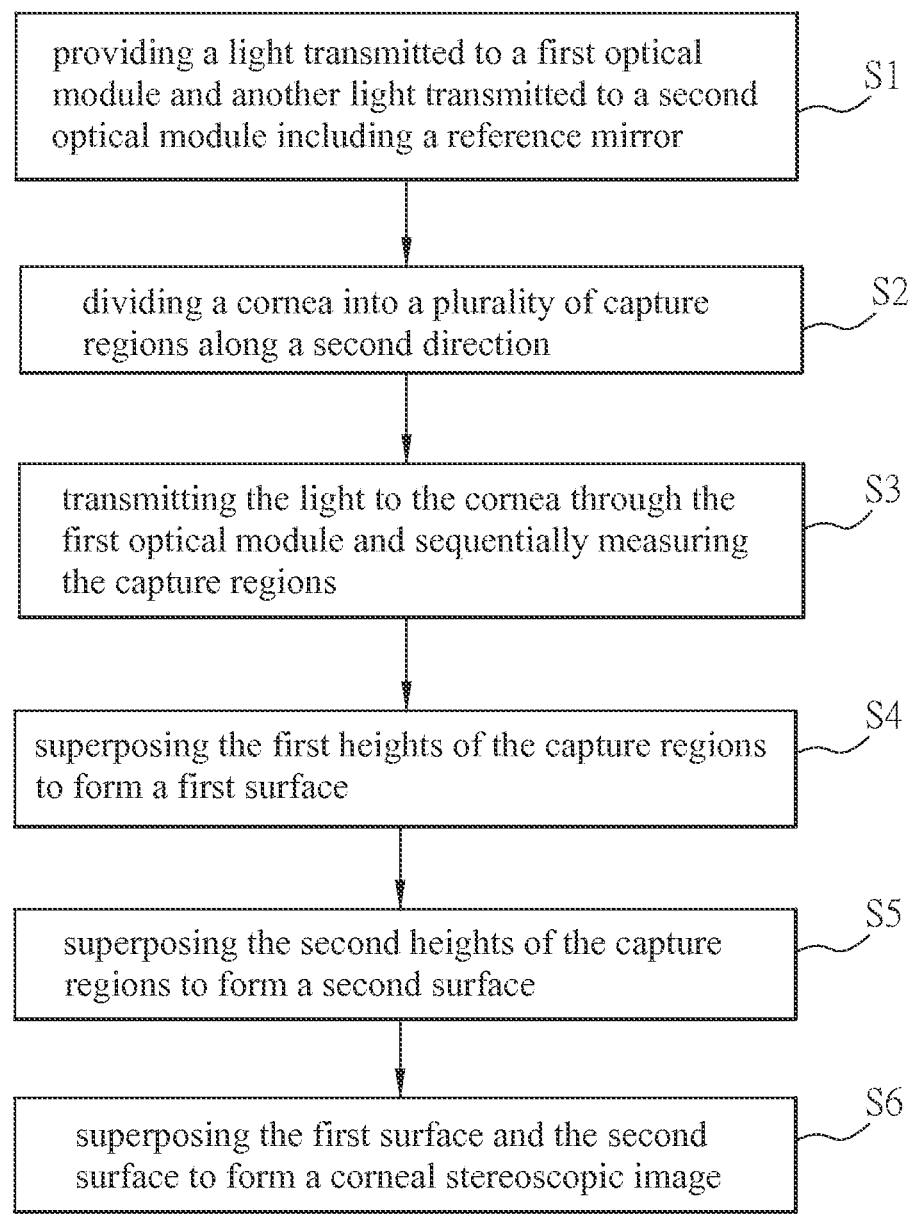
FIG. 3A is a schematic flowchart of a method for the corneal measuring according to an embodiment of the invention.
Figure 3B:
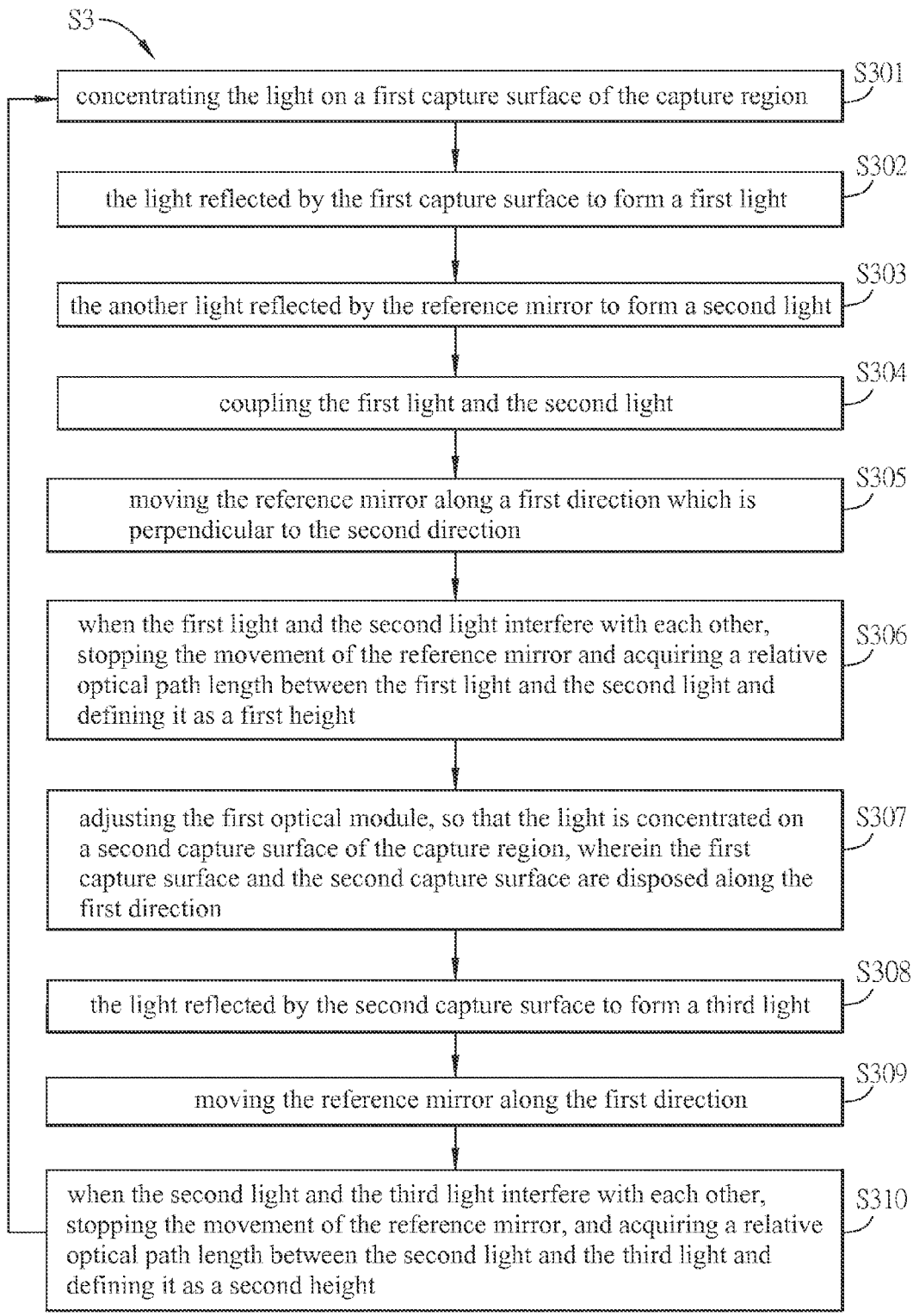
FIG. 3B is a schematic flowchart showing the detailed steps of the step S3 in FIG. 3A.
Figure 4:
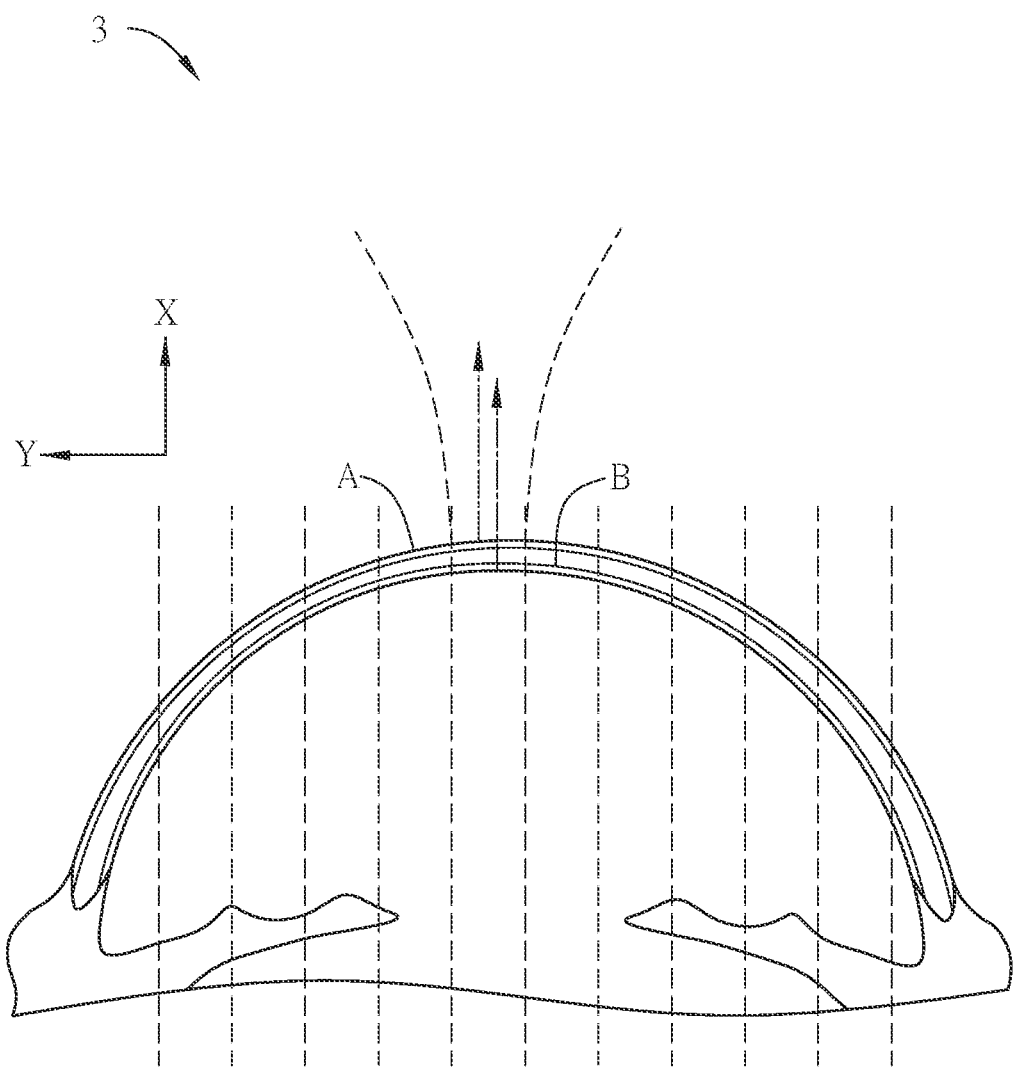
FIG. 4 is a schematic side-view diagram of the cornea.

The measurement and the superposition of the relative optical path length for making the corneal profile will be illustrated as below. FIG. 3A is a schematic flowchart of a method for the corneal measuring according to an embodiment of the invention, FIG. 3B is a schematic flowchart showing the detailed steps of the step S3 in FIG. 3A, and FIG. 4 is a schematic side-view diagram of the cornea. The optical device applied to the method of this embodiment can be the optical device 2 in FIG. 2, but this invention is not limited thereto.

As shown in FIG. 3A, a light can be provided first and is transmitted to the first optical module 22 and the second optical module 24 including the reference mirror 241 (step S1). Since the elements and operation of the first and second optical modules 22 and 24 can be comprehended by referring to the above embodiment, the related descriptions are omitted here for conciseness.

Then, the cornea 3 is divided into a plurality of capture regions along the second direction (Y direction) (step S2). In this embodiment, the cornea 3 can be divided into a plurality of capture regions along the second direction (Y direction), and the width of each of the capture regions is between 0.1 μm and 0.25 μm for example. Besides, the width of the capture region can be adjusted as less than a quarter of the light wavelength. Hence, if the light with the wavelength of 1030nm is used, the width of the capture region is at least less than 0.25 μm. Moreover, the total measuring time for the capture regions is about between 200 ms and 500 ms.

The quantity of the total captured image in this embodiment will be changed with different frame rates or image refresh rates of the camera. Basically, the quantity of the total captured image will be the product of the frame rate or image refresh rate and the captured time. In this embodiment, there are 250 captured images totally for example.

To be noted, the vertical dotted line in FIG. 4 just shows the possible capture manner, and the ratio and interval thereof are just for the illustrative purpose.

Then, the light is transmitted to the cornea 3 through the first optical module 22, and the capture regions are measured sequentially (step S3).

Subsequently, the first heights of the capture regions obtained in the step S3 are superposed to form the first surface (step S4), and the second heights of the capture regions obtained in the step S3 are superposed to form the second surface (step S5). Then, the first surface and the second surface are superposed together to form the stereoscopic image of the cornea 3 (step S6).

The step S3 will be further illustrated as below. The measuring steps of this embodiment can further include concentrating the light on the first capture surface A of the capture region (step S301). In this embodiment, the upper surface of the corneal epithelium of the cornea 3 can be defined as the first capture surface A for example. Besides, each of the capture regions has a first capture surface A.

Then, the light is reflected by the first capture surface A to form the first light (step S302). At the same time, the light transmitted to the second optical module 24 will be reflected by the reference mirror 241 to form the second light (step S303).

Then, the first light and the second light are coupled together (step S304). The coupling method of this step can be performed by the above-mentioned light splitter 26 or other equivalent light-combining elements. The coupled first and second lights will enter the image analysis unit 28 for the following analysis.

Then, the reference mirror 241 can be moved along the first direction (X direction) that is perpendicular to the second direction (Y direction) (step S305). The purpose of this step is to make the phase difference between the first and second lights an integer multiple by moving the reference mirror 241 so that the interference can be formed.

When the first light and the second light interfere with each other, the movement of the reference mirror 241 is stopped and the relative optical path length (OPD) between the first and second lights is captured and defined as the first height (step S306). Moreover, the first height here can be regarded as a height (thickness) from the upper surface of the corneal epithelium of the corresponding capture region to an imaginary reference surface. Moreover, other featured relative optical path lengths (OPD), such as maximum, average or minimum OPD, also can be captured in the corresponding capture region according to different standard or requirement and regarded as the first height of the corresponding capture region. In this embodiment, the maximum relative optical path length of the first and second lights is captured and regarded as the measurement basis for example.

Then, the first optical module 22 is adjusted, so that the light is concentrated on the second capture surface B (the lower surface of the corneal epithelium) of the capture region, and the first capture surface A and the second capture surface B are disposed along the first direction (X direction) (step S307). The light here is about concentrated on the single-layer endothelium of the cornea. Since the first capture surface A and the second capture surface B are disposed along the first direction (X direction), the first and second capture surfaces A and B can be construed to have a longitudinal relationship.

Likewise, the light is reflected by the second capture surface B to form the third light (step S308).

Then, the reference mirror 241 is moved along the first direction (X direction) (step S309). The purpose of this step is to make the phase difference between the third and second lights an integer multiple by moving the reference mirror 241 so that the interference can be formed.

When the second light and the third light interfere with each other, the movement of the reference mirror 241 is stopped and the relative optical path length between the second and third lights is captured and defined as the second height (step S310). The second height here can be regarded as a height (thickness) from the lower surface of the corneal epithelium of the corresponding capture region to an imaginary reference surface. Moreover, other featured relative optical path lengths (OPD), such as maximum, average or minimum OPD, also can be acquired in the corresponding capture region according to different standard or requirement and regarded as the second height of the corresponding capture region. In this embodiment, the maximum relative optical path length of the second and third lights is captured and regarded as the measurement basis for example.

In other words, the steps S301~S310 can be repeated for each of the capture regions to obtain the first and second heights thereof. Then, the first heights of the capture regions are superposed together to form the first surface (step S4) and the second heights of the capture regions are superposed together to form the second surface (step S5). Subsequently, the first surface and the second surface are superposed to form the corneal stereoscopic image (step S6).

Furthermore, in the steps S4 and S5, the interpolation method can be used to the superposition of the first heights and second heights to form the first surface and the second surface, respectively. For example, the interpolation method can be applied to the first heights (values of OPD) to obtain an interpolation function, then the curvature of the first surface can be acquired by the interpolation function, and the first surface can be plotted and formed accordingly. Likewise, the interpolation method can be applied to the second heights (values of OPD) to obtain another interpolation function, then the curvature of the second surface can be acquired by this interpolation function, and the second surface can be plotted and formed accordingly.

Because of the disposition of the capture regions, the lateral definition of the corneal stereoscopic image will not change (the definitions of the central region and surrounding region of the cornea won't change), and therefore the corneal image can get better quality. Besides, the shortcoming that the central region of the cornea can't be accurately measured in the conventional art by using the annular light source can be overcome.

Summarily, in this invention, due to the disposition of the light source module 20, first optical module 22, second optical module 24, light splitter 26 and image analysis unit 28 and the measurement with the longitudinal capture regions, the upper surface and lower surface of the corneal epithelium can be measured and therefore the optical device and method for the corneal stereoscopic image can be provided.

Furthermore, the optical device and method of this invention are not limited to the purpose of obtaining the disease result or healthy condition, but generates the corneal profile for the subsequent research and judgment basis of the diagnosis.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An optical device for corneal measuring, comprising:
    a light source module;
    a first optical module;
    a second optical module including a reference mirror;
    a light splitter through which the light provided by the light source module is transmitted to the first optical module and the second optical module; and
    an image analysis unit;
    wherein the light of the light source module is transmitted to a cornea through the light splitter and the first optical module and reflected by the cornea to form a first light, and the first light is sequentially transmitted to the light splitter and the image analysis unit, the light of the light source module is transmitted to the reference mirror of the second optical module through the light splitter and reflected by the reference mirror to form a second light, and the second light is sequentially transmitted to the light splitter and the image analysis unit, the reference mirror moves along a first direction, and when the first light and the second light interfere with each other, a relative optical path length is obtained.

2. The optical device as recited in claim 1, wherein the image analysis unit includes an image shooting unit.

3. The optical device as recited in claim 2, wherein the image shooting unit is a charge-coupled device (CCD) camera or a complementary metal-oxide-semiconductor (CMOS) camera.

4. The optical device as recited in claim 1, wherein the first optical module include a reflector and a lens, the light of the light source module is sequentially transmitted to the reflector and the lens of the first optical module through the light splitter.

5. The optical device as recited in claim 1, wherein the reference mirror is movable in a reciprocating manner.

6. The optical device as recited in claim 1, wherein the reference mirror is a non-spherical mirror or a lens coated with a film.

7. A method for corneal measuring, comprising steps of:
    providing a light transmitted to a first optical module and another light transmitted to a second optical module including a reference mirror;
    dividing a cornea into a plurality of capture regions along a second direction;
    transmitting the light to the cornea through the first optical module and sequentially measuring the capture regions, wherein the measuring steps include:
        concentrating the light on a first capture surface of the capture region;
        the light reflected by the first capture surface to form a first light;
        the another light reflected by the reference mirror to form a second light;
        coupling the first light and the second light;
        moving the reference mirror along a first direction which is perpendicular to the second direction;
        when the first light and the second light interfere with each other, stopping the movement of the reference mirror, and acquiring a relative optical path length between the first light and the second light and defining it as a first height;
        adjusting the first optical module, so that the light is concentrated on a second capture surface of the capture region, wherein the first capture surface and the second capture surface are disposed along the first direction;

the light reflected by the second capture surface to form a third light;

moving the reference mirror along the first direction; and when the second light and the third light interfere with each other, stopping the movement of the reference mirror, and acquiring a relative optical path length between the second light and the third light and defining it as a second height;

superposing the first heights of the capture regions to form a first surface;

superposing the second heights of the capture regions to form a second surface; and superposing the first surface and the second surface to form a corneal stereoscopic image.

8. The method for corneal measuring as recited in claim 7, wherein the step of superposing the first heights of the capture regions to form a first surface further include a step of:

superposing the first heights to form the first surface by an interpolation method.

9. The method for corneal measuring as recited in claim 7, wherein the step of superposing the second heights of the capture regions to form a second surface further include a step of:

superposing the second heights to form the second surface by an interpolation method.

10. The method for corneal measuring as recited in claim 7, wherein the width of the capture region is between 0.1 μm and 0.25 μm.

11. The method for corneal measuring as recited in claim 7, wherein the first optical module includes a reflector and a lens, and the light is transmitted to the reflector and the lens of the first optical module sequentially.

12. The method for corneal measuring as recited in claim 7, wherein the reference mirror is movable in a reciprocating manner.

13. The method for corneal measuring as recited in claim 7, wherein the reference mirror is a non-spherical mirror or a lens coated with a film.

* * * * *